(12) United States Patent
Chou et al.

(10) Patent No.: US 10,792,459 B2
(45) Date of Patent: Oct. 6, 2020

(54) VENTILATION APPARATUS AND USES THEREOF

(71) Applicant: Chang Gung Memorial Hospital, Linkou, Taoyuan (TW)

(72) Inventors: Pai-Chien Chou, Taoyuan (TW); Liu-Chieh Chou, Taoyuan (TW); Hui-Ju Yang, Taoyuan (TW)

(73) Assignee: Chang Gung Memorial Hospital, Linkou, Taoyuan (TW)

( * ) Notice: Subject to any disclaimer, the term of this patent is extended or adjusted under 35 U.S.C. 154(b) by 291 days.

(21) Appl. No.: 15/600,014

(22) Filed: May 19, 2017

(65) Prior Publication Data

US 2017/0333665 A1 Nov. 23, 2017

Related U.S. Application Data

(60) Provisional application No. 62/339,211, filed on May 20, 2016.

(51) Int. Cl.
*A61M 16/20* (2006.01)
*A61M 16/00* (2006.01)
(Continued)

(52) U.S. Cl.
CPC .............. *A61M 16/20* (2013.01); *A61H 31/02* (2013.01); *A61M 16/0009* (2014.02); *A61M 16/0051* (2013.01); *A61M 16/0057* (2013.01); *A61M 16/0072* (2013.01); *A61M 16/208* (2013.01); *F04B 5/02* (2013.01); *F04B 9/125* (2013.01); *F04C 21/002* (2013.01); *F04C 25/00* (2013.01); *A61H 9/00* (2013.01); *A61H 2201/107* (2013.01); *A61H 2201/1207* (2013.01); *A61H 2201/50* (2013.01); *A61H 2201/5071* (2013.01); *A61M 16/209* (2014.02); *A61M 2016/0027* (2013.01); *A62B 7/00* (2013.01)

(58) Field of Classification Search
CPC .......... A61M 16/0009; A61M 16/0051; A61M 16/0057; A61M 16/0072; A61M 16/208
See application file for complete search history.

(56) References Cited

U.S. PATENT DOCUMENTS 2,699,163 A * 1/1955 Engstrom ........... A61M 16/209
601/44
3,533,398 A * 10/1970 Jones ................... A61B 5/0935
346/72
(Continued)

FOREIGN PATENT DOCUMENTS

CN 103933648 A 7/2014
JP 2015500733 A 1/2015
(Continued)

*Primary Examiner* — Jason E Flick
*Assistant Examiner* — Tasnim Mehjabin Ahmed
(74) *Attorney, Agent, or Firm* — Pilloff Passino & Cosenza LLP; Sean A. Passino; Rachel K. Pilloff

(57) ABSTRACT

The present invention discloses ventilation apparatus, comprising a casing with a first vent and a second vent, a fixed spacer disposed within the casing, and a movable spacer in operative connection with a power mechanism. Also discloses herein are methods for ventilating a subject, by synchronously providing a positive pressure ventilation and a negative pressure ventilation using the ventilation apparatus described herein.

16 Claims, 5 Drawing Sheets

(51) Int. Cl.

| | |
|---|---|
| *F04B 5/02* | (2006.01) |
| *A61H 31/02* | (2006.01) |
| *F04C 21/00* | (2006.01) |
| *F04B 9/125* | (2006.01) |
| *F04C 25/00* | (2006.01) |
| *A61H 9/00* | (2006.01) |
| *A62B 7/00* | (2006.01) |

(56) References Cited

U.S. PATENT DOCUMENTS

| | | | |
|---|---|---|---|
| 5,086,767 A | | 2/1992 | Legal |
| 2005/0165334 A1 | * | 7/2005 | Lurie .................... A61M 16/06 |
| | | | 601/44 |
| 2009/0171256 A1 | | 7/2009 | Fiorina |
| 2014/0005566 A1 | | 1/2014 | Homuth et al. |

FOREIGN PATENT DOCUMENTS

| | | |
|---|---|---|
| JP | 2015157149 A | 9/2015 |
| TW | 201519919 A | 6/2015 |

\* cited by examiner

VENTILATION APPARATUS AND USES THEREOF

CROSS-REFERENCE TO RELATED APPLICATION

This application claims priority to U.S. Application No. 62/339,211, filed on 20 May 2016, the entire disclosure of which is incorporated herein by reference.

BACKGROUND OF THE INVENTION

1. Field of the Invention

The present invention relates to ventilation apparatus and methods of ventilating a subject, by synchronously deliver a positive pressure ventilation and a negative pressure ventilation to a subject in need thereof using the ventilation apparatus described herein.

2. Description of the Related Art

Mechanical ventilation refers to methods to mechanically assist a patient's breathing and/or replace the patient's spontaneous breathing, using a ventilator or a compression bag. Mechanical ventilation delivers two types of ventilation: (a) positive pressure ventilation, whereby air (or a gas mix) is pushed into the patient's upper airway and lung, and (b) negative pressure ventilation, whereby the patient's chest cavity expands to create sub-atmospheric pressure within the patient's lungs. The patient's lungs naturally recoil and expel the gas within in the absence of negative pressure ventilation.

Ventilators for patients requiring breathing assistance have traditionally been large, heavy, power-hungry devices that have provided little, if any mobility to a patient. Positive pressure ventilation alone is uncomfortable for the patient, cannot be used to clear the airway secretion and pushes air into less resistant lung space, which can lead to ventilation/perfusion mismatch. Negative pressure ventilation alone may cause upper airway collapse and compromises patient's airway. The use of two independent ventilators (a positive pressure ventilator generating positive pressure ventilation and a negative pressure ventilator generating negative pressure ventilation) to provide synchronized ventilation has shown limitations in efficacy and safety. For example, the positive pressure ventilator and the negative pressure ventilator may dyssynchronize over time. The inability of two separate ventilators to synchronously deliver and match the patient's flow demand can lead to serious complications, such as hypoxia, barotrauma, and prolonged mechanical ventilation time.

There is an unmet need to develop a ventilator to synchronously deliver a positive pressure ventilation and a negative pressure ventilation to patients with respiratory distress or requiring pulmonary rehabilitation. The present invention provides ventilators to satisfy these and other needs.

SUMMARY OF THE INVENTION

In one embodiment, the present invention provides ventilation apparatus, comprising a casing with a first vent and a second vent; a fixed spacer disposed within the casing; and a movable spacer in operative connection with a power mechanism, wherein the movable spacer and the fixed spacer divide the casing into a first space and a second space, wherein the first vent and the second vent are positioned on each side of the fixed spacer, and wherein the movable spacer rotate in a first direction and simultaneously generate a negative pressure in the first vent and a positive pressure in the second vent, and the movable spacer rotate in a reverse of the first direction and simultaneously reduce the negative pressure in the first vent and reduce the positive pressure in the second vent.

It is a further object of the invention to provide a ventilation apparatus, comprising a casing with a first vent and a second vent; a movable spacer in operative connection with a guiding device, wherein the movable spacer divide the casing into a first space and a second space, wherein the first vent and the second vent are positioned on each side of the movable spacer, and wherein the movable spacer moves in a first direction and simultaneously generate a negative pressure in the first vent and a positive pressure in the second vent, and the movable spacer moves in reverse of the first direction and simultaneously reduce the negative pressure in the first vent and reduce the positive pressure in the second vent.

In an embodiment, the ventilation apparatus further comprises a first conduit for coupling the ventilation apparatus to the chest of a subject and a second conduit for coupling the ventilation apparatus to the upper airway of a subject. Advantageously, the first conduit further comprises a pressure relief valve, a pressure sensor or a combination thereof; and/or the second conduit further comprises a gas supply mechanism, a pressure sensor, at least one pressure relief valve or a combination thereof.

In an embodiment, the ventilation apparatus further comprises a third conduit for coupling the first conduit to the second conduit, wherein the third conduit comprises an one way valve. Advantageously, the one way valve allows the pressure flow from the first conduit to the second conduit. Alternatively, the one way valve does not allow the pressure flow from the first conduit to the second conduit.

In an embodiment, the negative pressure is about 0 to −200 cm $H_2O$, and/or the positive pressure is about 0 to 200 cm $H_2O$.

In an embodiment, the volume of the first spacer or the second spacer is about 0.5 L to about 20 L.

Advantageously, the ventilation apparatus is substantially free of a controller to synchronize the delivery of a positive pressure and a negative pressure ventilation.

The present invention further discloses methods for ventilating a subject, comprising synchronize generating a positive pressure ventilation and a negative pressure ventilation using the ventilation apparatus described herein and delivering the negative pressure ventilation, the positive pressure ventilation or synchronize delivering the negative pressure and the positive pressure ventilation to the subject during the inhalation phase of the subject, are also provided.

In an embodiment, the method of ventilating a subject, comprises the steps of:
  synchronize generating a positive pressure ventilation and a negative pressure ventilation using a ventilation apparatus as disclosed above; and
  delivering the negative pressure ventilation, the positive pressure ventilation or synchronize delivering the negative pressure and the positive pressure ventilation to the subject during the inhalation phase of the subject In an embodiment, the ventilation apparatus as used comprises a first conduit for coupling the apparatus to the chest of the subject, a second conduit for coupling the ventilation apparatus to the upper airway of a subject, and a third conduit for coupling the first conduit and the second conduit, wherein the third conduit comprises an one way valve. Advantageously, the one way valve allows about 0 to 50 cm $H_2O$ of positive pressure flow from the first conduit to the second conduit during the exhalation phase of the subject.

In an embodiment, the method further comprises the step of delivering a positive pressure ventilation about 5 to 50 cm $H_2O$ to the upper airway of the subject during the exhalation phase of the subject. Advantageously, the negative pressure is about 0 to −200 cm $H_2O$ and/or wherein the positive pressure is about 0 to 200 cm $H_2O$.

In an embodiment, the delivering of the positive pressure ventilation, the negative pressure ventilation or synchronize delivering the negative pressure and the positive pressure ventilation takes about 0.5 to about 15 seconds.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

Illustrative embodiments of the present invention are described in detail below with reference to the following Figures.

DETAILED DESCRIPTION OF THE PREFERRED EMBODIMENTS

Figure 1A:
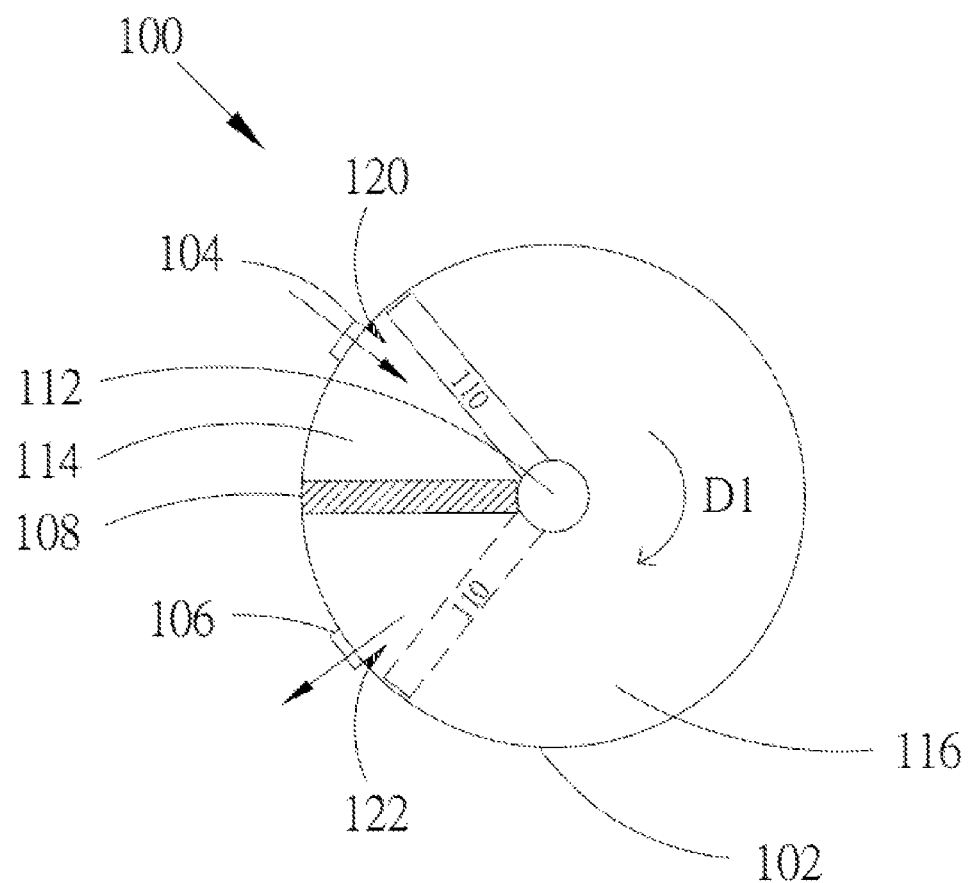
FIGS. 1A and 1B are top angle views of the ventilation apparatus 100 according to one embodiment of the present invention.

Hereinafter, embodiments of the present disclosure will be described in detail with reference to the accompanying drawings so that those skilled in the art to which the present disclosure pertains can realize the present disclosure. As those skilled in the art would realize, the described embodiments may be modified in various different ways, all without departing from the spirit or scope of the present disclosure.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be further understood that although the terms first and second are used herein to describe various elements, these elements should not be limited by these terms. These terms are only used to distinguish one element from another element.

For clarity and conciseness of the description, parts may be omitted from the drawings, and same reference characters or numerals may indicate identical parts or analogous parts. In the drawings, thicknesses of layers, films, panels, regions, etc., may be exaggerated for clarity and may not limit embodiments of the invention. If an element such as a layer, film, region, or substrate is referred to as being "on" another element, it can be directly on the other element, or an intervening element may be present.

The term "subject" can refer to a vertebrate who is in respiratory distress or in need of ventilation support. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

All numbers herein may be understood as modified by "about." In one embodiment, the term "about," when referring to a measurable value such as an amount, a temporal duration, and the like, is meant to encompass variations of ±10%, preferably ±5%, more preferably ±1%, and even more preferably ±0.1% from the specified value, as such variations are appropriate to the negative pressure, unless other specified. As used herein, the term "about," when referring to a range, is meant to encompass variations of ±10% within the difference of the range, preferably ±5%, more preferably ±1%, and even more preferably ±0.1% from the specified value, as such variations are appropriate to the negative pressure, unless other specified.

Figure 1B:
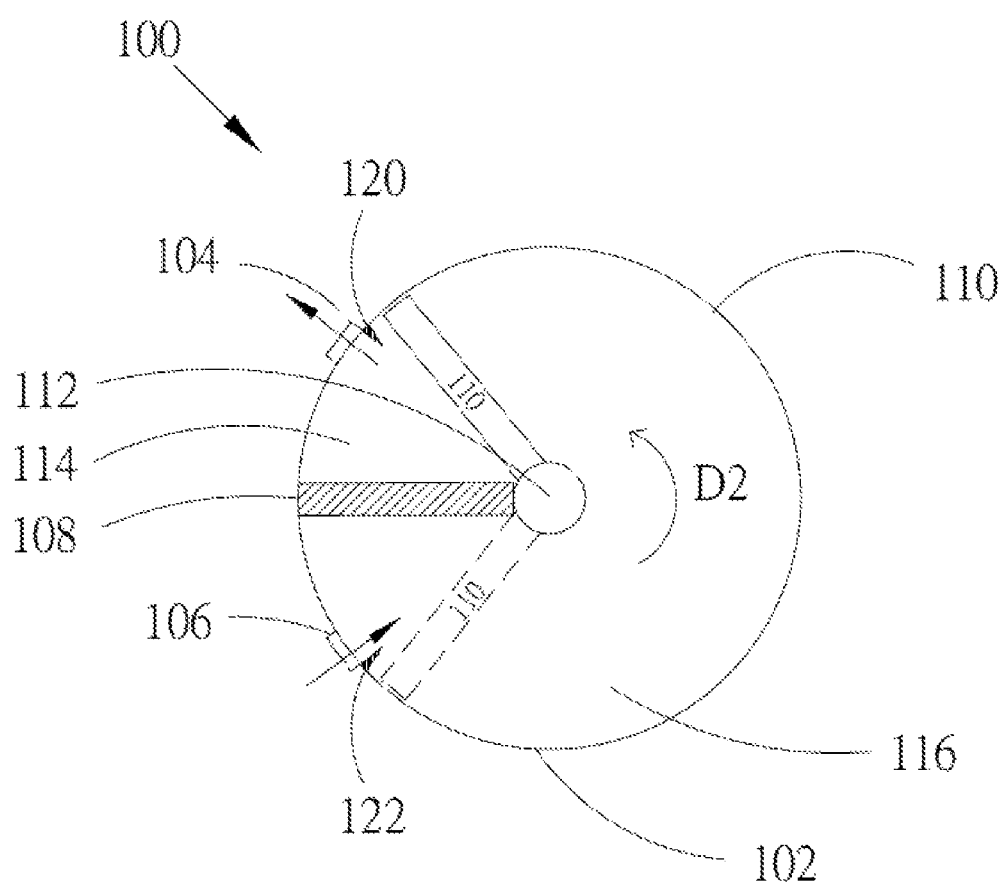

The present invention relates to a portable or wearable ventilation apparatus 100 to provide synchronized positive pressure and negative pressure ventilation to a subject, without a controller to synchronize the delivery of the positive and negative pressure ventilation. In one embodiment, as shown in FIG. 1A and FIG. 1B, the ventilation apparatus 100 comprises a casing 102 with a first vent 104 and a second vent 106, a fixed spacer 108, a movable spacer 110 coupled to a power mechanism 112. In some embodiments, the casing 102 is substantially circular. The fixed spacer 108 is disposed within the casing 102, and together with the movable spacer 110, to divide the casing 102 into a first space 114 and a second space 116. There is no communication between the gas in the first space 114 and the second space 116 (i.e., the gas in the first space 114 does not move to the second space 116 and vice versa). In some embodiments, the fixed spacer 108 and the movable spacer 110 are rigid. In other embodiments, the fixed spacer 108 and the movable spacer 110 are flexible.

In one embodiment, the power mechanism 112 comprises at least one of the following: a gear set, an electric motor, or an adjustable speed drive for adjusting the speed of the electric motor. In another embodiment, one end of the movable spacer 110 may be coupled to the gear set and served as an axis, such that the movable spacer 110 is able to be rotated by the power mechanism 112 around the axis.

Referring to FIG. 1A, prior to the movable spacer 110 moving in the first (D1) direction, the pressure in the first space 114 and in the second space 116 may be the same as the atmospheric pressure. Based on Boyle's law, as the movable spacer 110 rotates in the first (D1) direction (i.e., from the first space 114 toward the second space 116), the gas in the second space 116 is compressed and a positive pressure is generated therein to maintain a subject's upper airway. At the same time, the first space 114 expands and a negative pressure is generated therein to expand the subject's chest cavity or lung. In one embodiment, the rotation of the movable spacer 110 in the first (D1) direction corresponds to the inspiration phase of the subject.

In one embodiment, as the movable spacer 110 reaches a stopper 122 prior to or at the second vent 106, the first pressure relief valve 210 in the first conduit (depicted in FIG. 2) and the second pressure relief valve 214 in the second conduit (depicted in FIG. 2) open simultaneously for gas equilibration. This reduces the negative pressure in the first space 114 and/or first vent 104 and the positive pressure in the second space 116 and/or second vent 106, respectively. In one embodiment, the pressure in the first space 116 and/or first vent 104 reach atmospheric pressure after the opening of the first pressure relief valve 210. In an exemplary embodiment, the pressure in the first space 114 and/or the first vent 104 is measured by a pressure sensor 104A. In another embodiment, the pressure in the second space 116 and/or second vent 106 reach atmospheric pressure after the opening of the second pressure relief valve 214. This is followed by the rotation of the movable spacer 110 in reverse of the first direction (in D2 direction, from the second space 116 to the first space 114), as shown in FIG. 1B. In other embodiments, as the movable spacer rotates in D2 direction, the first pressure relief valve 212 and the second pressure relief valve 214 remain open so the pressure in the first space 114, the first vent 104, the second space 116 and/or second vent 106 during the D2 rotation remains at atmospheric pressure. In one embodiment, the rotation of the movable spacer 110 in reverse of the first (D1) direction (i.e., moving in D2 direction) corresponds to the expiration phase of the subject. In an exemplary embodiment, the pressure in the second space 116 and/or the second vent 106 is measured by a pressure sensor 106A. In another exemplary embodiment, the pressure sensor 104A and pressure sensor 106A are in communication with the movable spacer 110. According to the input from pressure sensors 104A and 106A, the pressure in the first space 114 and/or the first vent 104 as well as the pressure in the second space 116 and/or the second vent 106 can be adjusted by altering the rotation of the movable spacer 110.

Figure 2:
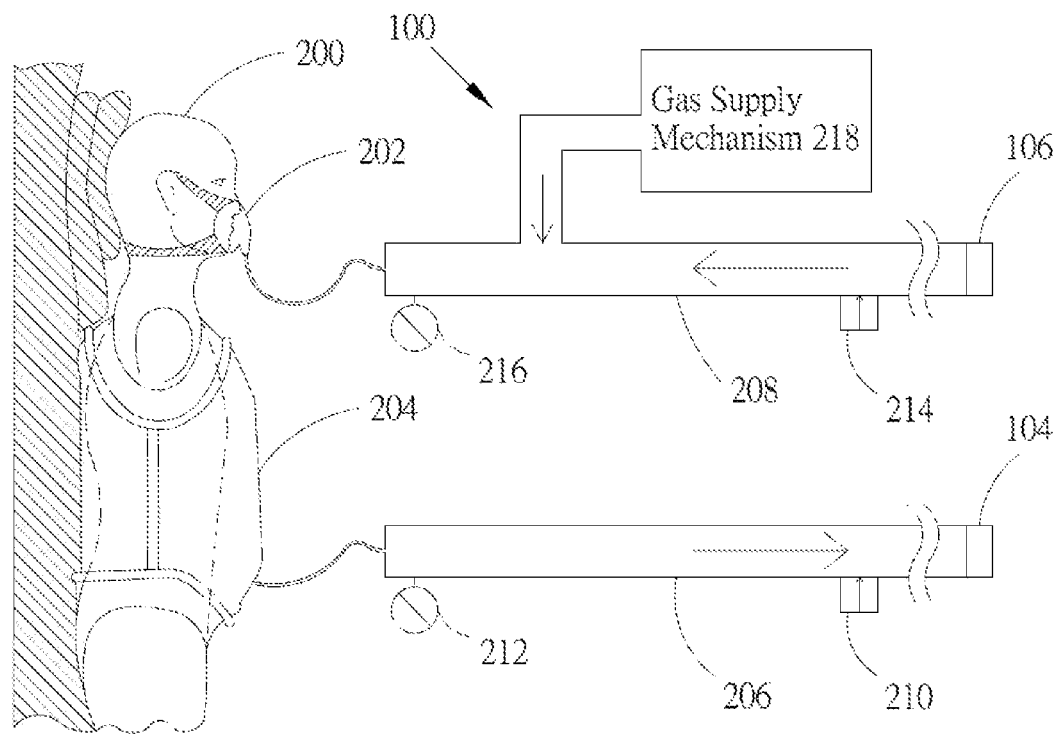
FIG. 2 illustrates schematically the connection of the first conduit and the second conduit of the ventilation apparatus 100 to a subject.

FIG. 2 illustrates the connection of the ventilation apparatus of the present invention to a subject 200 requiring ventilation assistance. The ventilation apparatus 100 further comprising a first conduit 206 for coupling the ventilation apparatus (e.g., the first vent 104) to the subject's chest or thorax and a second conduit 208 for coupling the ventilation apparatus (e.g., the second vent 106) to the upper airway (e.g., the face and the mouth) of the subject. In one embodiment, the first conduit 206 is coupled to the subject's chest using an enclosure device 204 selected from a body tank system, a chest cuirass, a body wrap, or a combination thereof. In an exemplary embodiment, the enclosure device 204, together with the ventilation apparatus provide sufficient negative pressure to expand the subject's chest cavity or lungs. In one embodiment, the second conduit is 208 is coupled to the subject's upper airway using a mask 202. Non limiting examples of the mask 202 include leak proof mask, oral CPAP mask and the full face mask. In an exemplary embodiment, the mask 202, together with the ventilation apparatus 100 provide sufficient positive pressure to open and maintain the subject's upper airway.

In some embodiments, a first pressure sensor 212 and/or a first pressure relief valve 210 are disposed in the first conduit 206. In an exemplary embodiment, the first pressure sensor 212 is in close proximity to the subject 200. In other embodiments, a second pressure sensor 216 and/or a second pressure relief valve 214 are disposed in the second conduit 208. In an exemplary embodiment, the second pressure sensor 216 is in close proximity to the subject 200. The first pressure sensor 212 and the second pressure sensor 216 are configured to monitor or measure the pressure in the first conduit 206 and the second conduit 208, respectively. Non limiting examples of the pressure sensor include pressure transducers, pressure transmitters, pressure senders, pressure indicators, piezometers and manometers. In some embodiments, the first 212 and second pressure sensors 216 are electronically connected and control the opening and closing of the first pressure relief valve 210 and the second pressure valve 214 respectively, so the pressure within the first conduit 206 and the second conduit 208 are maintained at a predetermined range.

In some embodiments, a gas supply mechanism 218 is connected to the second conduit 208. The gas from the gas supply mechanism 218 (for example, oxygen) is delivered to the second conduit 208 and mixed with the gas from the second space 116 (for example, room air) while the movable spacer 110 rotates in the first direction (D1 as shown in FIG. 1A). In other embodiment, the positive pressure generated in the second conduit 208 delivers the oxygen from the gas supply mechanism 218 to the upper airway of the patient 200, thereby increase oxygen supply to the subject.

Figure 3:
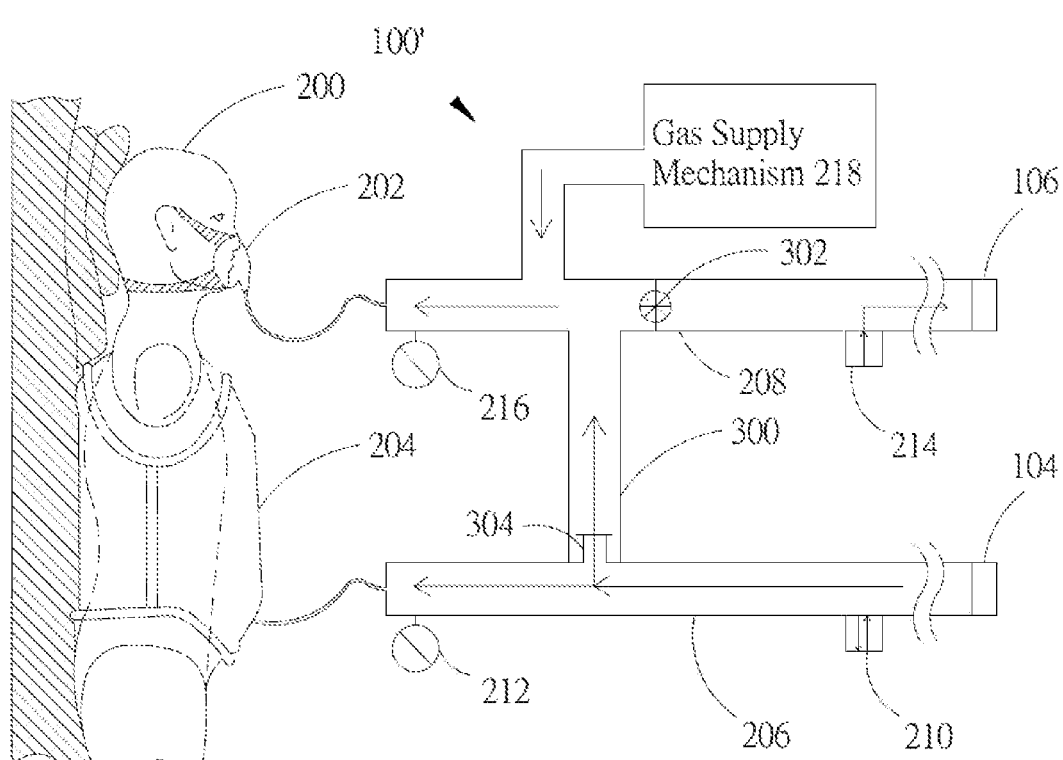
FIG. 3 illustrates schematically the connection of the first conduit, the second conduit and the third conduit of the ventilation apparatus 100 to a subject.

FIG. 3 illustrates another embodiment of the ventilation apparatus 100 of the present invention, wherein the ventilation apparatus 100 further comprising at least one of the following: a third conduit 300 connecting the first conduit 206 and the second conduit 208, a two way pressure relief valve 302 in the second conduit 208 or a one way pressure relief valve 304 in the third conduit 300, wherein the one way pressure relief valve 304 is in close proximity to the first conduit 206. In an exemplary embodiment, the gas supply mechanism 218 is proximal to the subject compare to the two way relief valve 302.

In certain embodiments, continuous positive pressure in the second conduit 206 is contemplated, such as when the subject 200 requires cardiopulmonary resuscitation (CPR) or sputum clearance. In an exemplary embodiment, continue positive pressure in the second conduit 208 is achieved as follows: during the inspiratory phase of the breathing cycle, the movable spacer 110 rotates in the first direction (D1) to generate a positive pressure in the second space 116 and second conduit 208. As soon as the movable spacer 110 reaches the stopper 122 prior to or at the second vent 106, the first pressure relief valve 210 in the first conduit 206 opens so the negative pressure generated in the enclosure device 204, the first space 114 and the first conduit 206 during the D1 rotation was equilibrated to atmospheric pressure. Similarly, the second pressure relief valve 214 in the second conduit 208 opens so the positive pressure generated in the second space 116 and the second conduit 208 during the D1 rotation was equilibrated to atmospheric pressure. In one embodiment, in which positive pressure in the first conduit 206 is required, as soon as the pressure in the first conduit 206 is reduced or reaches the atmospheric pressure, detected by the first pressure sensor 212, the first pressure relief valve 210 and the two way pressure relief valve 302 in the second conduit 208 are closed. In another embodiment, in which positive pressure in the first conduit 206 is not required, as soon as the pressure in the second conduit 208 is reduced or reaches the atmospheric pressure, detected by the second pressure sensor 216, the two way pressure relief valve 302 in the second conduit 208 is closed while the first pressure relief valve 210 remains open. In some embodiments, the second pressure relief valve 214 remained open during the D2 rotation/expiration phase. As the movable spacer 110 rotates in D2 direction, the pressure in the first space 114 and the first conduit 206 increases to a point wherein the pressure in the first conduit 206 (detected by the first pressure sensor 212) is higher than that in the second conduit 208 (detected by the second pressure sensor 216), the one way pressure relief valve 304 opens to allow about 5 to about 50 cm $H_2O$ of the positive pressure in the first conduit 206 pass through the third conduit 300 to the second conduit 208 and the subject's upper airway. As the movable spacer 110 reaches the stopper 120 prior to or at the first vent 104, the first pressure relief valve 210 opens again for gas equilibration so the positive pressure generated in the first space 114 and the first conduit 206 during the D2 rotation/expiration phase was reduced, until the pressure therein reaches the atmospheric pressure. In one embodiment, the two way pressure relief valve 302 in the second conduit 208 opens as the movable spacer 110 reaches the stopper 120 prior to or at the first vent 104. The movable spacer 110 again rotates in the first direction (D1) to correspond to the subject's inspiration phase, as described in the preceding paragraphs.

By rotating the movable spacer 110 in a first (D1) direction and in reverse (D2) to the first direction described herein, in combination with a third conduit 300 to continuously provide about 5 to about 200 cm $H_2O$ to the second conduit 208, CPR or sputum clearance can be performed. In one embodiment, the continuous positive pressure in the second conduit 208 maintains the subject's upper airway as well as the continuously supply of a desirable gas (e.g., oxygen) to the subject, while the intermittent positive pressure in the first conduit 206 compresses the subject's chest cavity, to increase cardiac output or expel secretion. The continuous positive pressure in the second conduit 208 and in the upper airway of the subject is an advantage compare to the manual CPR, which provides intermittent positive pressure to the subject's upper airway.

The frequency of the CPR can be adjusted by adjusting the speed of the movable spacer 110 rotation. In one embodiment, during advance cardiac life support, the positive pressure (about 5 to about 200 cm $H_2O$) is transferred from the first conduit 210 to the third conduit 300 and the second conduit 208 twice with every 30 chest compressions by providing the positive pressure to the enclosure device 204.

In one embodiment, the effect of the movable spacer 110, the first pressure relief valve 210, the second pressure relief valve 214, and the two way valve in the second conduit 302 on the pressure of the first conduit 206 and the second conduit 208 is shown in Table 1 and Table 2.

TABLE 1

The effect of the movable spacer, the pressure relief valves on the pressure in first conduit and second conduit during synchronized pressured ventilation

| Subject's breathing Cycle | Movable spacer 110 | Pressure in 1st conduit | Pressure in 2nd conduit | 1st pressure relief valve 210 | 2nd pressure relief valve 214 | Valve in 2nd conduit 302 |
|---|---|---|---|---|---|---|
| Inspiration | Starts at the stopper 120 in the first vent | Atmospheric pressure | Atmospheric pressure | X | X | ○ |
| | Ends at the stopper 122 in the second vent | Maximum negative pressure | Maximum positive pressure | X | X | ○ |
| Expiration | At the stopper 122 in the second vent | Atmospheric/ a lowered negative pressure | Atmospheric/ a lowered positive pressure | ○ | ○ | ○ |
| Expiration | Starts at the stopper 122 in the second vent | Atmospheric/ a lowered negative pressure | Atmospheric/ a lowered positive pressure | ○ | ○ | ○ |
| | Ends at the stopper 120 in the first vent | Atmospheric pressure | Atmospheric pressure | ○ | ○ | ○ |

X indicates the valve is closed
○ indicates the valve is opened

TABLE 2

The effect of the movable spacer, the pressure relief valves on the pressure in first conduit, second conduit and third conduit.

| Subject's breathing Cycle | Movable spacer 110 | Pressure in 1st conduit | Pressure in 2nd conduit | 1st pressure relief valve 210 | 2nd pressure relief valve 214 | Valve in 2nd conduit 302 |
|---|---|---|---|---|---|---|
| Expiration phase | At the stopper 122 in the second vent | Atmospheric pressure | Atmospheric pressure/ pre-set pressure * | ◯ | ◯ | X |
| | Move towards the stopper 120 in the first vent | Increasing positive pressure | Atmospheric pressure/ pre-set pressure * | X | ◯ | X |
| | At the stopper 120 in the first vent | Maximum positive pressure | Atmospheric pressure/ pre-set pressure * | X | ◯ | X |
| Inspiration phase | At the stopper 120 in the first vent | Atmospheric pressure | Atmospheric pressure/ pre-set pressure * | ◯ | ◯ | ◯ |
| | Move towards the stopper 122 in the second vent | Increasing Negative pressure/ atmospheric pressure | Increasing positive pressure/ pre-set pressure * | X/◯ | X | ◯ |
| | At the stopper 122 in the second vent | Maximum negative pressure/ atmospheric pressure | Maximum positive pressure/ pre-set pressure * | X/◯ | X | ◯ |

X indicates the valve is closed
◯ indicates the valve is opened
* pre-set pressure is about 5, 6, 7, 8, 9, 10 cm H$_2$O or any range of value therebetween In one embodiment, the positive pressure generated by the ventilation apparatus of the present invention ranges from about 0 to about 200 cm H$_2$O. In an exemplary embodiment, the lower limit of the positive pressure is equal to or greater than about 10, 11, 12, 13, 14, 15, 16, 17, 18, 19, or 20 cm H$_2$O or any value or range of values therebetween in 0.1 cm H$_2$O increments (e.g., about 15.2 cm H$_2$O, about 12.1 cm H$_2$O). In another exemplary embodiment, the upper limit of the positive pressure is equal to or less than about 200, 199, 198, 197, 196, 195, 194, 193, 192, 191, 190 cm H$_2$O or any value or range of values therebetween in 0.1 cm H$_2$O increments (e.g., about 195.2 cm H$_2$O, about 192.1 cm H$_2$O). In another embodiment, the positive pressure is a range of pressure between the lower limit and the upper limit of the positive pressure recite herein, such as 12 cm H$_2$O to 200 cm H$_2$O, 13.2 cm H$_2$O to 199.5 cm H$_2$O.

In some embodiments, the negative pressure generated by the ventilation apparatus of the present invention ranges from about 0 to about −200 cm H$_2$O. In an exemplary embodiment, the lower limit of the negative pressure is equal to or greater than about −10, −11, −12, −13, −14, −15, −16, −17, −18, −19, or −20 cm H$_2$O or any value or range of values therebetween in 0.1 cm H$_2$O increments (e.g., about −15.2 cm H$_2$O, about −12.1 cm H$_2$O). In another exemplary embodiment, the upper limit of the negative pressure is equal to or less than about −200, −199, −198, −197, −196, −195, −194, −193, −192, −191, −190 cm H$_2$O or any value or range of values therebetween in 0.1 cm H$_2$O increments (e.g., about −196.3 cm H$_2$O, about −198.4 cm H$_2$O). In another embodiment, the negative pressure is a range of pressure between the lower limit and the upper limit of the negative pressure recite herein, such as −12 cm H$_2$O to −200 cm H$_2$O, −13.2 cm H$_2$O to −199.5 cm H$_2$O.

In other embodiments, the negative pressure and the positive pressure of the ventilation apparatus 100 can be calculated according to the Boyle's equation P1*V1=P2*V2. In one exemplary embodiment, before the movable spacer 110 moves in the first direction (D1), P1 in the first spacer 114 is atmospheric pressure (1033.23 cm H$_2$O) and V1 is the lung volume of the subject (about 3 L). As the movable spacer 110 rotates in the first direction until it reaches the stopper at the second vent, V2=3 L (lung capacity of the subject)+3 L (volume of the enclosure device 204)=6 L and the calculated P2=P1*V1/V2=501.67 cm H$_2$O. Hence, the maximum negative pressure Pnm=P2-atmospheric pressure=−501.67 cmH$_2$O. In another exemplary embodiment, before the movable spacer 110 moves in the D2 direction (i.e., the reverse of the first direction), P1' is atmospheric pressure (1033.23 cmH$_2$O) and V1'=3 L (volume of the enclosure device 204)+3 L (the lung capacity of the patient)=6 L. As the movable spacer 110 rotates in reverse of the first direction until it reaches the stopper at the first vent, V2' is the lung volume=3 L and the calculated positive pressure P2'=P1'*V1'/V2'=2066 cm H$_2$O. Hence, the maximum positive pressure Ppm=P2'-atmospheric pressure=2066-1033 cmH$_2$O=1033 cmH$_2$O.

In one embodiment, the rotation of the movable spacer 110 in the first direction (D1) and in the reverse direction (D2) is one breathing cycle and each breathing cycle takes about 0.5 to about 15 seconds. The frequency of each breathing cycle ranges from 4 per minutes to 60 per minutes, and can be adjusted according to the subject's age or physical condition.

Figure 4A:
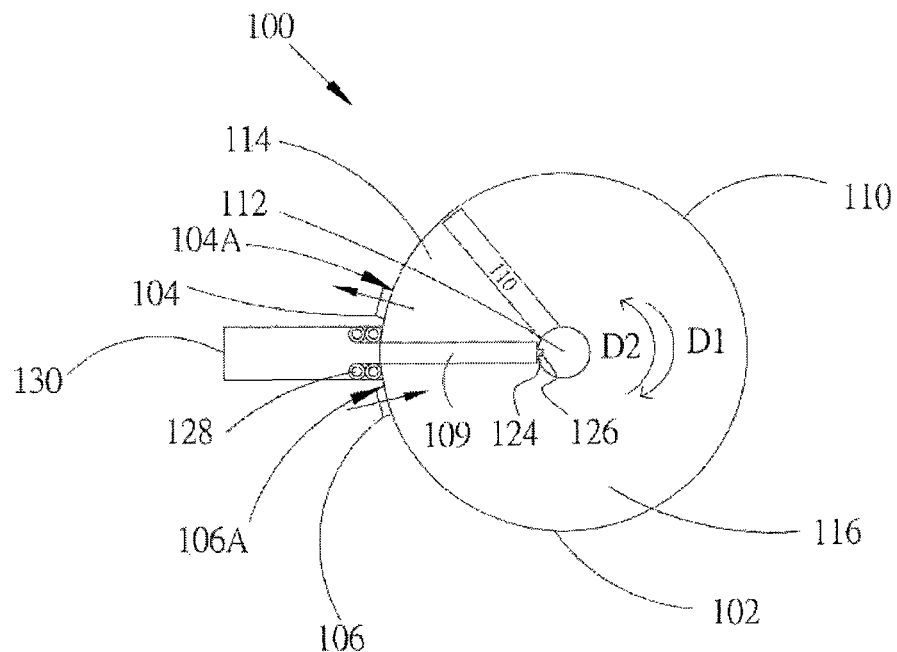
FIG. 4A and FIG. 4B are top angle views of the ventilation apparatus 100 according to the second embodiment of the present invention.

In another embodiment, referring to FIG. 4A, the ventilation apparatus comprises a movable spacer 110 and a second spacer 109 within the casing 102. One end of the second spacer 109 is fixed to the power mechanism 112. In one exemplary embodiment, the second spacer 109 comprises an engagement part 124 and the power mechanism 112 comprises a recess 126. The second spacer 109 is fixed to the power mechanism 112 by inserting the engagement part 124 into the recess 126 of the power mechanism. The movable spacer 110 and the second spacer 109 divide the ventilation apparatus into a first space 114 and a second space 116.

Figure 4B:
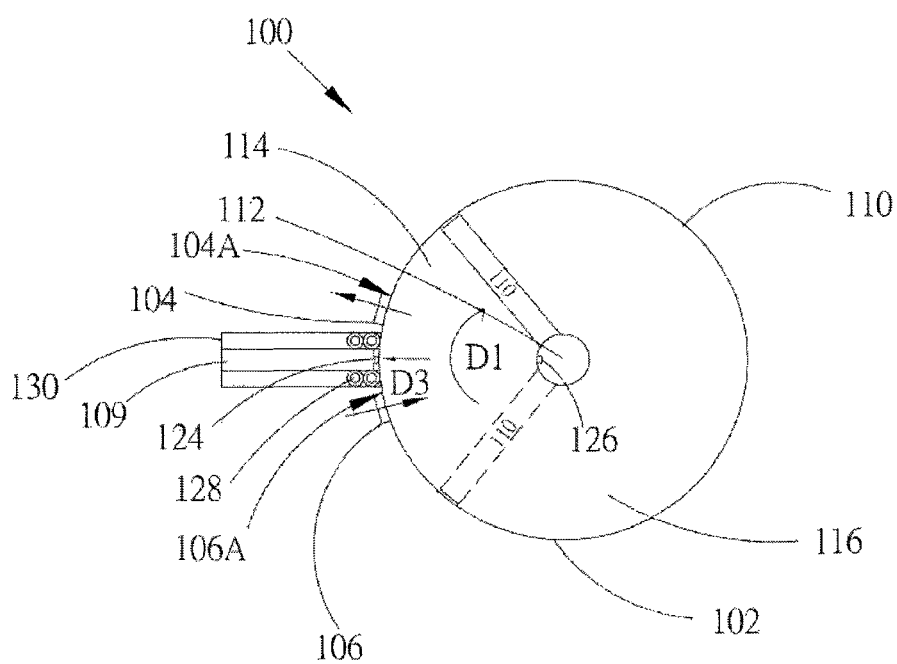

In one embodiment, the movable spacer 110 moves in the D1 direction (to generate positive pressure in the second vent 106 and negative pressure in the first vent 104) and passes the second vent 106. Just before the movable spacer 110 reaches the second spacer 109, said second spacer 109 will withdraw from the casing 102. In one exemplary embodiment, the second spacer 109 withdraws from the casing by sliding into the placing slot 130 via the transmission shafts 128, as illustrated FIG. 4 B. As the second spacer withdraws from the casing 102, the movable spacer 110 continues to move in the D1 direction and reaches the first vent 104. The second spacer 109 is connected to the power mechanism 112 once again so the movable spacer 110 continues to move in the D1 direction to generate negative pressure in the first vent 104 and positive pressure in the second vent 106.

Figure 5A:
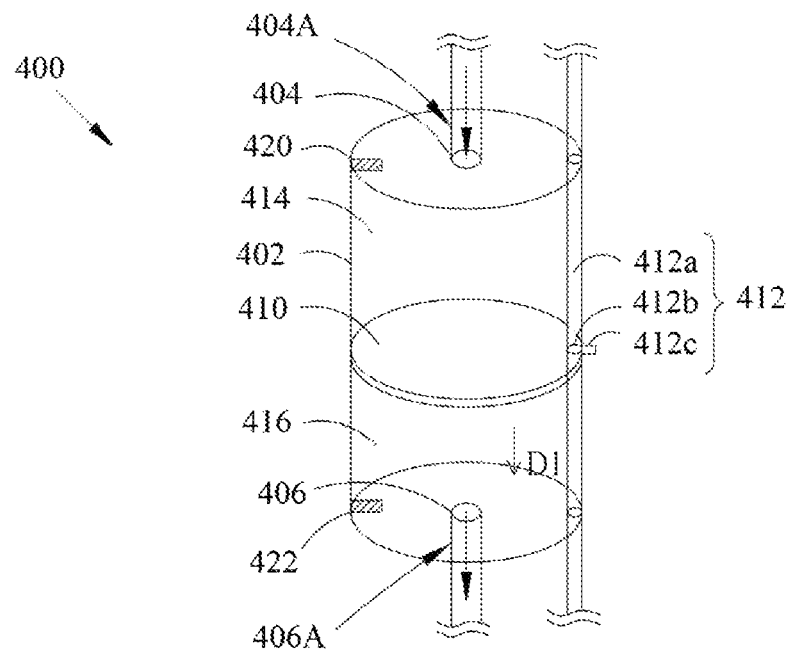
FIG. 5A and FIG. 5B are the horizontal cross section views of the ventilation apparatus 100 according to the third embodiment of the present invention.
Figure 5B:
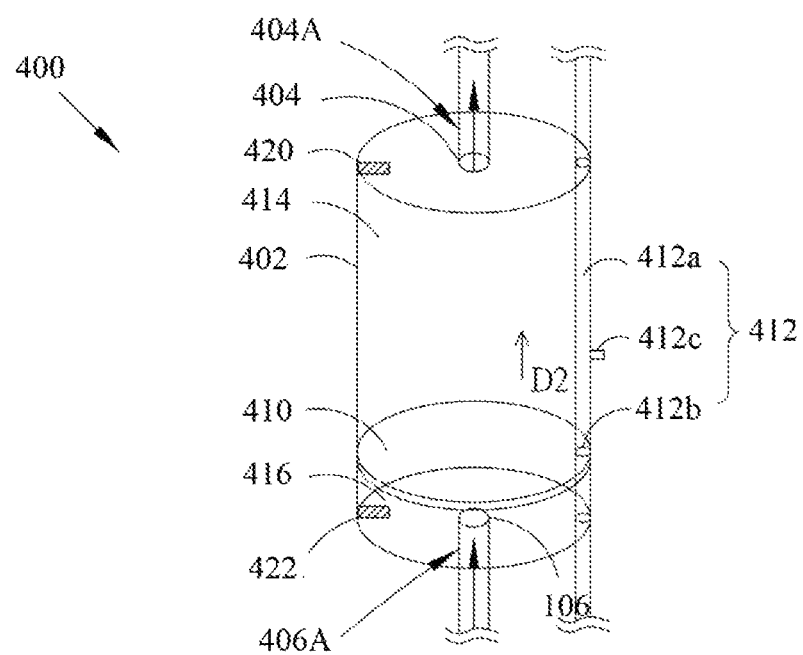

FIG. 5A and FIG. 5B illustrate a third embodiment of a ventilation apparatus 400 of the present invention, comprising a first vent 404, a second vent 406, a casing 402, a movable spacer 410 in operative connection to a guiding device 412. In an exemplary embodiment, the casing 402 is substantially tubular. The cross section of the casing 402 can be substantially circular, substantially oval, or any shape. The movable spacer 410 is within the casing 402, dividing the casing 402 into a first space 414 and a second space 416.

There is no communication between the gas in the first space 414 and the second space 416 (i.e., the gas in the first space 414 does not move to the second space 416 and vice versa). In some embodiments, the movable spacer 410 is substantially rigid. In other embodiments, the movable spacer 410 is substantially flexible.

In some embodiments, the guiding device 412 comprises one or more guiding rails 412a to longitudinally slide the movable spacer 410 in D1 or D2 direction. In a preferred embodiment, the movable spacer 410 has an insertion hole 412b for the guiding rail 412a to passes through. The guiding rail 412a includes one or more conveying structures to move the movable spacer 410 in D1 or D2 direction. Non limiting examples of the conveying structure include a motor 412c, an inverted tooth chain, or a conveyor belt.

Prior to the movable spacer move in D1 direction, the pressures in the first space 414 and the second space 416 are equal to the atmospheric pressure. When the movable spacer moves in D1 direction (i.e., from the first space 414 toward the second space 416), the gas in the second space 416 is compressed and a positive pressure is generated therein to maintain a subject's upper airway. At the same time, the first space 414 expands and a negative pressure is generated therein to expand the subject's chest cavity or lung. In one embodiment, the sliding of the movable spacer 410 in the first (D1) direction corresponds to the inspiration phase of the subject.

In one embodiment, as the movable spacer 410 reaches the second vent 406 or a stopper 422, the first pressure relief valve 210 in the first conduit (as depicted in FIG. 2) and the second pressure relief valve 214 in the second conduit (depicted in FIG. 2) open simultaneously for gas equilibration. This reduces the negative pressure in the first space 414 and/or first vent 404 and the positive pressure in the second space 416 and/or second vent 406, respectively.

In one embodiment, the pressure in the first space 416 and/or first vent 404 reach atmospheric pressure after the opening of the first pressure relief valve 210. In an exemplary embodiment, the pressure in the first space 414 and/or the first vent 404 is measured by a pressure sensor 404A. In another embodiment, the pressure in the second space 416 and/or second vent 406 reach atmospheric pressure after the opening of the second pressure relief valve 214. This is followed by the rotation of the movable spacer 410 in reverse of the first direction (in D2 direction, from the second space 416 to the first space 414), as shown in FIG. 5B.

In other embodiments, as the movable spacer slides in D2 direction, the first pressure relief valve 212 and the second pressure relief valve 214 remain open so the pressure in the first space 414, the first vent 404, the second space 416 and/or second vent 406 during the D2 sliding remains as atmospheric pressure. In one embodiment, the sliding of the movable spacer 410 in D2 direction corresponds to the expiration phase of the subject.

In another exemplary embodiment, the pressure sensor 404A and pressure sensor 406A are in communication with the movable spacer 410. According to the input from pressure sensors 404A and 406A, the pressure in the first space 414 and/or the first vent 404 as well as the pressure in the second space 416 and/or the second vent 406 can be adjusted by altering the rotation of the movable spacer 410.

The ventilation apparatus described herein present, amongst others, the following features:
1. Synchronously deliver a positive pressure ventilation and a negative pressure ventilation to a subject without any time lag;
2. A small casing and a simple power mechanism are required, making the device portable and affordable; and
3. An optional third conduit can be used to perform CPR, by synchronously providing positive pressure in the first conduit and the second conduit.

While the disclosure has been described by way of example and in terms of the preferred embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:
1. A ventilation apparatus, comprising:
   a casing with a first vent and a second vent;
   a fixed spacer disposed within the casing; and
   a movable spacer in operative connection with a power mechanism,
   a first conduit for coupling the first vent to the chest of a subject and a second conduit for coupling the second vent to the upper airway of the subject,
   wherein the movable spacer and the fixed spacer divide the casing into a first space and a second space,
   wherein the first vent and the second vent are positioned on each side of the fixed spacer, and
   wherein the movable spacer rotate in a first direction and simultaneously generate a negative pressure in the first vent and a positive pressure in the second vent, and the movable spacer rotate in reverse of the first direction and simultaneously deliver a positive pressure ventilation in the first vent and a negative pressure ventilation in the second conduit, wherein the negative pressure ventilation is configured to create a sub-atmospheric pressure within the subject's upper airway or lung.

2. The ventilation apparatus of claim 1, comprising at least one of the following:
  (a) the first conduit further comprising a pressure relief valve, a pressure sensor or a combination thereof; or
  (b) the second conduit further comprising a gas supply mechanism, a pressure sensor, at least one pressure relief valve or a combination thereof.

3. The ventilation apparatus of claim 1, further comprising a third conduit for coupling the first conduit and the second conduit, wherein the third conduit comprises a one way valve.

4. The ventilation apparatus of claim 3, wherein the one way valve allows the pressure flow from the first conduit to the second conduit.

5. The ventilation apparatus of claim 1, wherein the negative pressure is about 0 to −200 cm $H_2O$, wherein the positive pressure is about 0 to 200 cm $H_2O$.

6. The ventilation of apparatus of claim 1, wherein the volume of the first space or the second space is about 0.5 L to about 20 L.

7. The ventilation apparatus of claim 1, wherein the ventilation apparatus is substantially free of a controller to synchronize the delivery of a positive pressure and a negative pressure ventilation.

8. A method of ventilating a subject, comprising the steps of:
  synchronize generating a positive pressure ventilation and a negative pressure ventilation using the ventilation apparatus of claim 1; and
  synchronize delivering the negative pressure and the positive pressure ventilation to the subject during the inhalation phase of the subject.

9. The method of claim 8, comprising at least one of the following:
  (a) the first conduit further comprising a pressure relief valve, a pressure sensor, or
  (b) the second conduit further comprising a gas supply mechanism, a pressure sensor, at least one pressure relief valve or a combination thereof.

10. The method of claim 8, wherein the ventilation apparatus further comprising a third conduit for coupling the first conduit and the second conduit, wherein the third conduit comprises a one way valve.

11. The method of claim 10, wherein the one way valve allows about 0 to 50 cm $H_2O$ of positive pressure flow from the first conduit to the second conduit during the exhalation phase of the subject.

12. The method of claim 8, further comprising the step of delivering a positive pressure ventilation about 5 to 50 cm $H_2O$ to the upper airway of the subject during the exhalation phase of the subject.

13. The method of claim 8, wherein the negative pressure is about 0 to −200 cm $H_2O$.

14. The method of claim 8, wherein the positive pressure is about 0 to 200 cm $H_2O$.

15. The method of claim 8, wherein synchronize delivering the negative pressure and the positive pressure ventilation takes about 0.5 to about 15 seconds.

16. The method of claim 8, wherein the ventilation apparatus is substantially free of a controller to synchronize the delivery of a positive pressure and a negative pressure ventilation.

* * * * *